United States Patent [19]

Kricsfalussy et al.

[11] Patent Number: 5,233,072
[45] Date of Patent: Aug. 3, 1993

[54] PROCESS FOR THE PREPARATION OF DIALKYL CARBONATES

[75] Inventors: Zoltan Kricsfalussy; Helmut Waldmann; Hans-Joachim Traenckner, all of Leverkusen; Marko Zlokarnik, Cologne; Reinhard Schomäcker, Leverkusen, all of Fed. Rep. of Germany

[73] Assignee: Bayer Aktiengesellschaft, Leverkusen, Fed. Rep. of Germany

[21] Appl. No.: 976,627

[22] Filed: Nov. 16, 1992

[30] Foreign Application Priority Data

Nov. 26, 1991 [DE] Fed. Rep. of Germany ....... 4138755

[51] Int. Cl.$^5$ .............................................. C07C 69/96
[52] U.S. Cl. .................................................... 558/277
[58] Field of Search ........................................ 558/277

[56] References Cited

U.S. PATENT DOCUMENTS

| | | | |
|---|---|---|---|
| 3,846,468 | 11/1975 | Perotti et al. | 558/275 |
| 4,218,391 | 8/1980 | Romano et al. | 558/277 |
| 5,142,087 | 8/1992 | Joerg et al. | |

FOREIGN PATENT DOCUMENTS

| | | |
|---|---|---|
| 0413215 | 8/1990 | European Pat. Off. |
| 2110194 | 3/1971 | Fed. Rep. of Germany |
| 2743690 | 9/1977 | Fed. Rep. of Germany |

OTHER PUBLICATIONS

Japanese Patents Reports, vol. R., No. 17, p. 5, of JP-45/11129 (1970).

*Primary Examiner*—Mary C. Lee
*Assistant Examiner*—Michael G. Ambrose
*Attorney, Agent, or Firm*—Sprung Horn Kramer & Woods

[57] ABSTRACT

To prepare $C_1$–$C_4$-dialkyl carbonates, $C_1$–$C_4$-alkanols are reacted with CO and $O_2$ at a relatively high temperature in a salt melt containing Cu salts.

19 Claims, No Drawings

PROCESS FOR THE PREPARATION OF DIALKYL CARBONATES

BACKGROUND OF THE INVENTION

1. Field of the Invention

The invention relates to an improved process for the preparation of dialkyl carbonates.

Dialkyl carbonates, in particular dimethyl carbonate, are intermediate products which have a low toxicity, and can replace toxic intermediate products, such as phosgene or dimethyl sulphate, in many reactions. It is furthermore non-corrosive. No environmentally harmful by-products are formed when it is used.

Examples of such reactions of dialkyl carbonates are the preparation of urethanes from aliphatic or aromatic amines, which in turn can be split to give the corresponding isocyanates. Dimethyl carbonate, for example, can also replace dimethyl sulphate in the quaternisation of amines or in the methylation of phenol or of naphthols. Dimethyl carbonate furthermore can be added to petrol for cars as an agent which improves the octane rating, for example instead of lead compounds. In view of this importance of dialkyl carbonates, there is still a lack of an industrially simple and environmentally compatible production process which is suitable for large capacities without substantial formation of by-products or linked substance circulations.

2. Description of the Related Art

There are various preparation processes for the preparation of dialkyl carbonates which have also already been tried industrially on a small scale. The preparation routes based on the catalytic reaction of alkanols with carbon monoxide and oxygen in accordance with the following equation have been worked on intensively by various study groups:

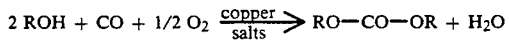

$$2\ ROH + CO + 1/2\ O_2 \xrightarrow[\text{salts}]{\text{copper}} RO-CO-OR + H_2O$$

The copper compounds which act as the catalyst have thus been employed in the form of various copper salts. When copper(II) chloride is used as the catalyst in accordance with JP-45/11129 (1970), unsatisfactory selectivities are achieved. Trouble is caused above all by the formation of relatively large amounts of methyl chloride, which, because of its great volatility, tends to spread ubiquitously in the entire production plant and can cause corrosion practically in the entire plant.

A better selectivity is obtained when organic complexing agents are used (DE-A 2,110,194), but here there is the problem of separating off the catalyst salts, which are partly dissolved in the reaction mixture but to a greater extent are present as a suspension.

Carrying out this reaction in accordance with DE-A 2,743,690 especially presents problems, since the catalyst salts are practically completely undissolved in the reaction mixture but merely suspended. These salts must be conveyed through the reaction zone and through the cooling units, and separated off mechanically, for example with the aid of centrifuges, after the reaction. In addition to the corrosion already mentioned, this also causes erosion, poor heat transfer as well as blockages and encrustations.

In order to avoid these disadvantages of a catalyst circulation, it has been proposed to keep the catalyst salts suspended in stationary form in the reactor and to meter methanol, CO and oxygen into the reactor, while the dialkyl carbonate formed and the water of reaction are distilled off from the reactor, together with the methanol employed in excess (EP 0,413,215 A2). The liquid reaction medium here essentially comprises the alkanol to be reacted (EP-0,413,215, page 3, line 52), so that the molar ratio between the alkanol and the Cu salt is very high (preferably 1:0.01–0.05). This has the disadvantage that the rate of reaction is relatively low. The need to establish a low dialkyl carbonate concentration also presents problems here. This is not easy, since the reaction is carried out under a high system pressure, and the solubilities of the dialkyl carbonate and also of the water in the reaction medium, which essentially comprises methanol, are very high. This means that removal of the dialkyl carbonate and water must be forced with a relatively large amount of inert gas or methanol gas.

Moreover, with this proposal it is to be expected that after some time the catalyst must be exchanged or a certain proportion of it must be constantly renewed, which is associated with the abovementioned problem of removal, regeneration and recycling of the catalyst.

SUMMARY OF THE INVENTION

In contrast, it has now been found that the reaction of $C_1$–$C_4$-alkanols with carbon monoxide and oxygen to give $C_1$–$C_4$-dialkyl carbonates can be carried out without these problems if the $C_1$–$C_4$-alkanol, CO and $O_2$ are reacted at 120°–300° C., preferably at 120°–180° C., particularly preferably at 120°–150° C., in a salt melt containing Cu salts.

DETAILED DESCRIPTION OF THE INVENTION

Possible alkanols are methanol, ethanol, propanol, isopropanol, n-butanol and sec-butanol. Methanol and ethanol are preferred, and methanol is particularly preferred.

The reaction is carried out in a salt melt containing Cu salts, possible Cu salts being Cu(I) and Cu(II) compounds and mixtures thereof. In principle, all known Cu salts are suitable if they are merely soluble in the salt melt to a certain extent.

In addition to the halides, such as, for example, the chlorides or the bromides, the cyanides, thiocyanates, sulphates, nitrates, carbonates, acetates, formates, oxalates and alcoholates, for example Cu methoxychloride, are also suitable. Cu can also be employed in the form of complexed compounds, such as the acetylacetonates, or Cu-N complexes, such as Cu-pyridine complexes or Cu-dipyridyl complexes.

Mixtures of salts which have a low melting point, that is to say form a eutectic, are in general used for the salt melt. It is therefore advantageous to use proportions of the salts corresponding to the composition of the eutectic. Such eutectics can be formed by Cu salts with one another or by Cu salts and other salts.

In addition to the Cu salts, it is therefore in principle possible to use all salts which are chemically inert, or also catalytically active in the context of the invention, that is to say which reduce the activation energy for the oxycarbonylation of alkanols. In addition to Cu salts, a large number of salts or salt-like compounds can be used here. As a rule, mixtures of Cu salts and such salt-like compounds are employed. The halides of main and sub-groups 1–3 are preferably employed. The chlorides of the alkali metals, such as NaCl or KCl, or chlorides of the alkaline earth metals, such as $CaCl_2$ or $MgCl_2$, as well as ZnCl₂, are particularly suitable. However, it is also possible to use less common compounds, such as the chlorides of thallium, indium or gallium.

A particularly suitable melt comprises, for example, Cu(I) chloride and KCl in various proportions. In general, mixtures having a high content of Cu compounds, for example a weight ratio of Cu(I) chloride to KCl of 60–70 to 40–30, are chosen.

The reaction temperature is in general about 120° C. to 300° C., preferably 120° C. to 180° C., and typical reaction temperatures are 120° C.–150° C.

The reaction can be carried out under normal pressure. To obtain a sufficiently high rate of reaction, however, it is advantageous to carry out the reaction under increased pressure, for example under 5–50 bar, preferably under 10–30 bar, particularly preferably under 15–25 bar.

The molar ratios of the reaction components employed are important for the rate of reaction and for the selectivity of the reaction. If these relationships are not taken into account, for example, the dimethyl acetal of formaldehyde or—which is particularly troublesome—methyl chloride occur as by-products.

In general, a molar excess of methanol in relation to carbon monoxide and in turn an excess of carbon monoxide in relation to oxygen, but at most molar amounts of CO and $O_2$, are chosen. Molar ratios of alkanol to CO and $O_2$ of 1:(1–0.01):(1–0.01), preferably 1:(0.5–0.02):(0.3–0.02), are thus chosen. This results in a methanol conversion of, for example, 10–50% and a CO conversion 10–80%. Oxygen is in general reacted completely. The explosion limits must of course be observed when metering in the quantities. If appropriate, the reaction can be carried out in the presence of inert gases, such as $N_2$ or $CO_2$.

However, it is likewise possible to carry out the reaction with a molar excess of CO with respect to methanol.

Thus, for example, a molar ratio of alkanol:CO of 1:1–50 can be chosen.

A particularly suitable mixture results at a molar ratio of 1:15.

The oxygen can be employed, for example, in the form of atmospheric air or air enriched with $O_2$.

The unreacted contents of methanol and CO can be recycled after the dialkyl carbonate and $H_2O$, and if appropriate $CO_2$, have been separated off.

The process according to the invention can be carried out in the various known types of reactor. For example, it can be carried out in a stirred kettle with a gassing stirrer. The process can be carried out discontinuously or also continuously. Reaction kettle cascades having, for example, 3–5 reactors are also suitable for the continuous procedure. However, a one- or multi-stage bubble column is also suitable for the process.

The gas loading can be varied within wide limits, depending on the pressure and temperature, so that space/time yields of between 10 and 200 g/l×hour can be achieved.

The heat of reaction can be removed by cooling units. In a particular embodiment, however, the reaction is carried out in a so-called boiling reactor in which the heat of reaction is removed by evaporating product. Thus, for example, when alkanol is fed in as a liquid, the heat of reaction is taken up by evaporation of the alkanol; cooling units are not necessary on the reactor here. In this case, the reaction products of dialkyl carbonate and water are discharged from the reactor by the stream of gas. The concentration of the substances in the stream of gas depends on the pressure and temperature. It may therefore be advantageous, especially under a higher pressure, to let down the reactor briefly and then to operate it again under pressure (so-called pressure swing technique). For the preparation of dimethyl carbonate, for example, a procedure can thus be followed in which the reaction is carried out under a higher pressure, for example under 25–50 bar, for 1 to 10 minutes and the system pressure is then reduced to about 10 to 1 bar. The melt remains completely in the reaction zone here, and the organic substances, for example dimethyl carbonate and methanol, are distilled out of the reactor practically completely. This cyclic change in the system pressure, which facilitates removal of the reaction products, is particularly suitable for the process according to the invention.

The life of the salt melt is long. During continuous operation, a part stream, for example 0.01–5% of the salt melt per hour, can be pumped out and regenerated separately. The regeneration can be carried out by careful burning off with air or by dissolving in water, extraction of the aqueous phase and evaporation of the raffinate to dryness.

Suitable materials for the reactors are, for example, corrosion-resistant stainless steels, steel enamels, glass or special metals, such as tantalum.

EXAMPLE 1

376 ml of a salt mixture, melted at 150° C., of 72% of Cu(I) chloride and 28% of KCl were initially introduced into a 1000 ml steel stirred tank which was provided with a Ta insert and fitted with a gassing stirrer and pressure-maintaining device. 250 g/hour of methanol, 24 l/hour of CO and 57.0 l/hour of air were metered in.

At a conversion of 9.75 % of methanol, dimethyl carbonate was obtained in a space/time yield of 54.2 g/l ×hour with a selectivity of 85.7%.

EXAMPLE 2

The following results were obtained in the same apparatus as in Example 1 with rhythmic letting down to 5 bar at intervals of about 5 minutes:

| T °C. | P bar | $O_2$ % by volume | Conversion of $CH_3OH$ % | SEL DMC % | SEL formal % | SEL $CH_3Cl$ % |
|---|---|---|---|---|---|---|
| Pressure swing technique: | | | | | | |
| 150 | 25 | 4.43 | 9.75 | 85.7 | 12.7 | 1.6 |
| 150 | 25 | 2.48 | 7.50 | 94.7 | 4.8 | 0.5 |
| 150 | 25 | 1.32 | 2.20 | 98.7 | 1.3 | 0 |

SEL = selectivity (... to ...)
DMC = dimethyl carbonate
formal = dimethylformal

EXAMPLE 3

94 ml of a salt mixture, melted at 150° C., of 72% of Cu(I) chloride and 28% of KCl were initially introduced into a 1000 ml steel tank which was provided with a Ta insert and fitted with an inlet and outlet line, pressure-maintaining device and temperature measuring device. 380 g/hour of methanol, 36 l/hour of CO and 43 l/hour of air were metered in under a total pressure of 50 bar. After the tank had been let down, dimethyl carbonate was obtained in a space/time yield of 210 g/(l×hour) and a selectivity of 96.5% at a conversion of 7.2% of methanol.

What is claimed is:

1. A process for the preparation of a $C_1$-$C_4$-dialkyl carbonate, wherein a $C_1$-$C_4$-alkanol, CO and $O_2$ are reacted at 120°–300° C. in a salt melt containing Cu salts.

2. The process of claim 1, wherein the temperature is 120°–180° C.

3. The process of claim 2, wherein the temperature is 120°–150° C.

4. The process of claim 1, wherein methanol, ethanol, n-propanol, isopropanol or n-butanol is employed as the $C_1$-$C_4$-alkanol.

5. The process of claim 4, wherein methanol or ethanol is employed as the alcohol.

6. The process of claim 5, wherein methanol is employed as the alcohol.

7. The process of claim 1, wherein CU(I) or Cu(II) salts or mixtures of Cu(I) and Cu(II) salts in the form of the halides, cyanides, sulphates, nitrates, nitrites, carbonates, acetates, formates, oxalates or alcoholates, or in the form of complex compounds, are employed as the Cu salts.

8. The process of claim 7, wherein the Cu chlorides are employed as the Cu salt.

9. The process of claim 8, wherein Cu(I) chloride is employed as the Cu salt.

10. The process of claim 1, wherein other salts which form eutectics at between 120° and 300° C. with Cu salts are used for the salt melt.

11. The process of claim 1, wherein salt melts which contain, in addition to Cu salts, halides of the alkali metals, the alkaline earth metals, zinc, thallium, indium, or gallium are used.

12. The process of claim 11, wherein a mixture of Cu(I) chloride and KCl is used as the salt melt.

13. The process of claim 1, which is carried out under increased pressure.

14. The process of claim 13, which is carried out under a pressure of 5–50 bar.

15. The process of claim 14, which is carried out under a pressure of 10–30 bar.

16. The process of claim 1, wherein a molar ratio of alkanol to CO and $O_2$ of 1:(1–0.01):(1–0.01) is chosen.

17. The process of claim 16, wherein a molar ratio of alkanol to CO and $O_2$ of 1:(0.5–0.02):(0.3–0.02) is chosen.

18. The process of claim 1, wherein the reaction is carried out in reaction kettles provided with gassing stirrers or in a one- or multi-stage bubble column.

19. The process of claim 1, wherein the system pressure is changed cyclically.

* * * * *